United States Patent [19]

Le Paih et al.

[11] Patent Number: 5,539,544

[45] Date of Patent: Jul. 23, 1996

[54] HOLOGRAPHIC FILTER FOR PROTECTION FROM RADIATION, NOTABLY LASER RADIATION

[75] Inventors: Gérard Le Paih, Merignac; Jean B. Migozzi, Orsay, both of France

[73] Assignee: Sextant Avionique, Meudon La Foret, France

[21] Appl. No.: 290,090

[22] Filed: Aug. 15, 1994

Related U.S. Application Data

[63] Continuation of Ser. No. 16,087, Feb. 10, 1993, abandoned.

[30] Foreign Application Priority Data

Feb. 18, 1992 [FR] France .................. 92 01812

[51] Int. Cl.⁶ .................. G02B 5/32; G03H 1/00
[52] U.S. Cl. .................. 359/15; 359/8; 359/24; 359/568
[58] Field of Search .................. 359/1, 8, 15, 24, 359/568

[56] References Cited

U.S. PATENT DOCUMENTS

| | | | |
|---|---|---|---|
| 4,601,533 | 7/1986 | Moss | 359/24 |
| 4,637,678 | 1/1987 | Moss et al. | 359/15 |
| 4,830,441 | 5/1989 | Chang | 359/15 |
| 4,965,152 | 10/1990 | Keys et al. | 359/15 |
| 5,103,323 | 4/1992 | Magarinos et al. | 359/8 |
| 5,432,623 | 7/1995 | Egan et al. | 359/15 |
| 5,471,326 | 11/1995 | Hall et al. | 359/15 |
| 5,481,383 | 1/1996 | Morishima et al. | 359/15 |

FOREIGN PATENT DOCUMENTS

| | | |
|---|---|---|
| 442206 | 8/1991 | European Pat. Off. . |
| 2551224 | 3/1985 | France . |

OTHER PUBLICATIONS

Tedesco, Optical Engineering, vol. 28, No. 6, Jun. 1989, pp. 609–615. "Holographic Laser–protective filters and eyewear".

Magarinos, et al., Applied Optics, vol. 26, No. 13, Jul. 1987, pp. 2575–2581. "Holographic optical configurations for eye protection against lasers".

*Primary Examiner*—Paul M. Dzierzynski
*Assistant Examiner*—John Juba, Jr.
*Attorney, Agent, or Firm*—Oblon, Spivak, McClelland, Maier & Neustadt

[57] ABSTRACT

A holographic filter for protection from radiation, notably laser radiation. At least one support is covered with at least two holograms. Each hologram is constituted by a stack of strata. The holograms are fixed to each other by an optical bonder associated with a selective absorbent material.

10 Claims, 4 Drawing Sheets

5,539,544

HOLOGRAPHIC FILTER FOR PROTECTION FROM RADIATION, NOTABLY LASER RADIATION

This application is a continuation of application Ser. No. 08/016,087, filed on Feb. 10, 1993, now abandoned.

BACKGROUND OF THE INVENTION

1. Field of the Invention

The present invention relates to a holographic filter for protection from radiation, notably laser radiation. It can be applied especially to the making of glasses or visors to protect the eyes efficiently from a single-line or multiple-line laser illumination while at the same time providing for efficient transmission of the rest of the visible spectrum, so as to preserve the quality of comfortable viewing through the glasses or visors. More generally, it can be applied to the protection of any physical sensor that could be destroyed or damaged by radiation, for example laser-emitted radiation.

2. Description of the Prior Art

There are several existing solutions to the problem of attenuating radiation, for example by the absorption of one or more of their lines. The standard absorbent materials are not selective enough and any efficient system of protection causes considerable deterioration in the transmission of the rest of the visible spectrum. For example, to obtain protection from a given line and to obtain an attenuation that corresponds to a density of over 5, the entire visible spectrum becomes very greatly attenuated. The above-mentioned value of density, which expresses the attenuation of the line, implies that, in this case, only a part smaller than $10^{-5}$ of the energy of the line to be attenuated is transmitted. More generally, a density equal to n means that the energy transmitted through the absorbent material is equal to $10^{-n}$ of the energy received by this absorbent material.

The only selective absorbent materials known are those that let through the infrared, i.e. they filter only lines with a wavelength of less than about 520 nm, but these absorbent materials greatly reduce viewing quality, with the scene that is viewed having a yellow or even red appearance.

Another approach consists in using filtering devices made on the basis of thin layers. These layers are constituted by a stack of metal or dielectric layers representing a variation in index designed to deflect and reflect the light. In devices such as these, the width of the reflected spectral band is directly related to the angular field to be covered by the protective system. For example, if protection is envisaged for a wide angular field, of about 45° for example, against a laser line (532 nm for example), it is necessary, for a given angle of incidence, of 30° for example, to reflect a wide spectral band ranging from 490 nm to 570 nm, which causes deterioration in viewing quality. While this approach appears to be sufficiently selective as regards the angle of incidence, it is not so with respect to the wavelength.

Known approaches make it possible, in theory, to filter light rays selectively. However, their practical embodiments do not always give the expected results and are therefore not efficient.

The aim of the invention is to overcome the above-mentioned drawbacks, notably by enabling the selective and efficient filtering of one or more light rays on a wide angular range, while at the same time providing for efficient transmission of the rest of the visible spectrum.

SUMMARY OF THE INVENTION

To this end, an object of the invention is a holographic filter for the protection of a sensor from radiation, said filter comprising at least one support covered with at least two holograms, each hologram being constituted by a stack of strata or layers, wherein the holograms are fixed to one another by an optical bonder associated with a selective absorbent material.

The main advantages of the invention are that it notably provides for efficient protection of the eye or of any other sensor from laser rays and provides for viewing comfort when applied to glasses or visors for example.

BRIEF DESCRIPTION OF THE DRAWINGS

Other features and advantages of the invention will appear from the following description, made with reference to the appended drawings, of which.

MORE DETAILED DESCRIPTION

Figure 1A:
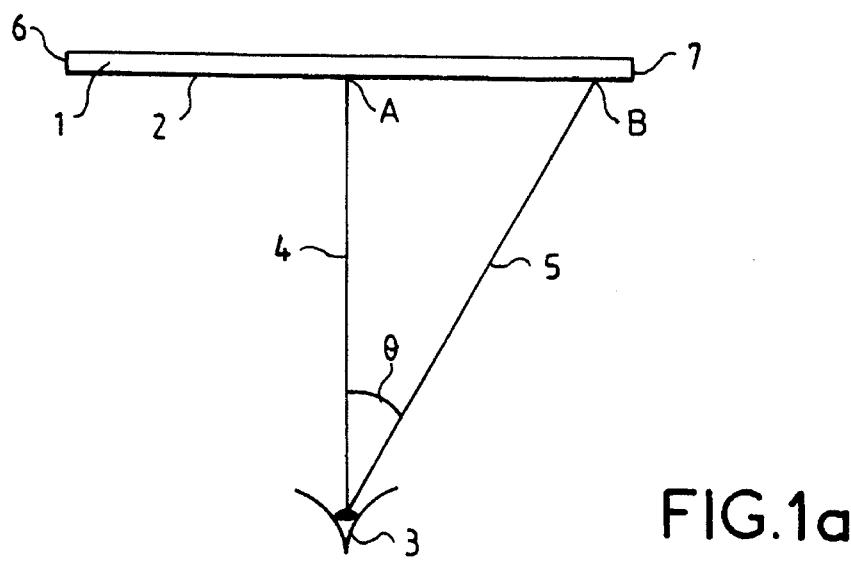
FIG. 1a shows the position of an eye or a sensor in relation to a filter.
Figure 1B:
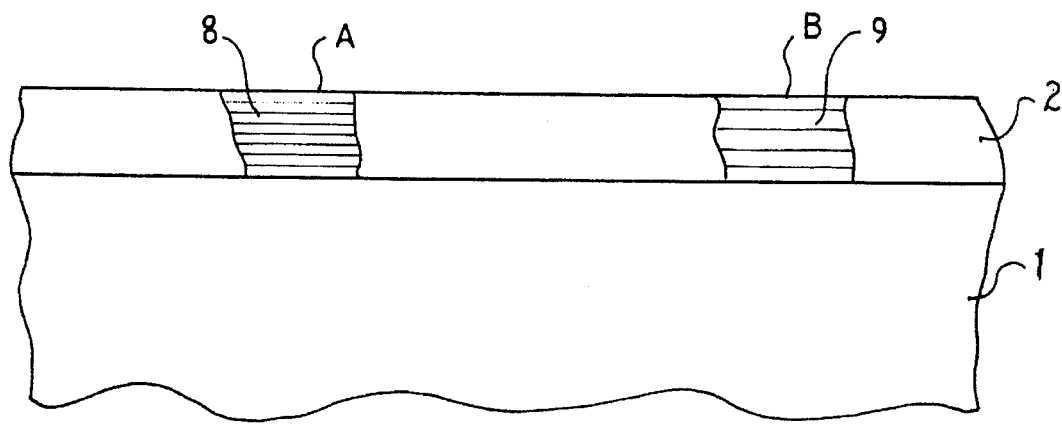
FIG. 1b shows an exemplary embodiment of a filter.

FIGS. 1a and 1b illustrate an example of a filter when the eye or the sensor remain fixed to the filter. In FIG. 1a, a light-transparent support 1, which may be plane, is covered by a hologram 2. This hologram 2 is seen by a human eye 3 or a sensor for example. The hologram 2 is formed by a stack of strata or layers. The refraction index of the hologram 2 has a refraction index modulation. The index varies periodically according to the thickness of the hologram recording material. The refraction index period of variation constitutes the spacing of the strata. This variation may be sinusoidal for example. The pitch is defined by the spacing of the strata layers.

In order to filter one or more optical lines selectively, the support 1 covered with the hologram 2 being at a substantially constant distance from the eye 3, the geometry of the strata varies according to the angle θ at which they are seen by the eye 3.

FIG. 1b shows an embodiment with a variation in the thickness of each strata layer of the hologram 2. The support 1 and the hologram 2 are chiefly enlarged in the direction of their thicknesses with respect to FIG. 1a. The geometry of the strata is represented as it is, for example, at a point A and at a point B of the hologram. The point A is seen by the eye 3 along a direction 4 perpendicular to the support 1 as can be seen in FIG. 1a while the point B is seen by the eye 3 along a direction 5 forming an angle θ with the above-mentioned direction 4. In the case of FIG. 1b, the difference in geometry between the strata 8 at the point A and the strata 9 at the point B relates to the variation of the pitch between these strata. If λ designates the wavelength of a line to be filtered at the point B and θ designates the angle of incidence of this line with respect to the normal of the hologram 2 on the support 1, the pitch of the strata of the hologram in the holographic recording material producing the reflection of the line on this material is given by Bragg's law:

$$p = \frac{\lambda}{2\cos\theta} \quad (1)$$

p designating the pitch

Thus, the filtering of the line is obtained by its reflection on the hologram.

For example, at the point A, $$p = \frac{\lambda}{2}$$

To protect the eye 3 or any other sensor from a radiation with a given wavelength in all the directions in which the eye sees the hologram 2 between the edges 6 and 7 of this hologram, the pitch of the strata may vary for example as a function of the angle θ at which they are seen according to the relationship (1) mentioned here above.

It would be possible to superimpose several filters with different pitches enabling the filtration of the different wavelengths on different angular zones.

One advantage of the filter illustrated in FIG. 1b is notably the fact that it is easy to record the hologram 2 by holographic methods known to those skilled in the art. However, preferably, the pitch of the strata should be defined with sufficient precision so that the filter made according to the invention is sufficiently selective.

Figure 2:
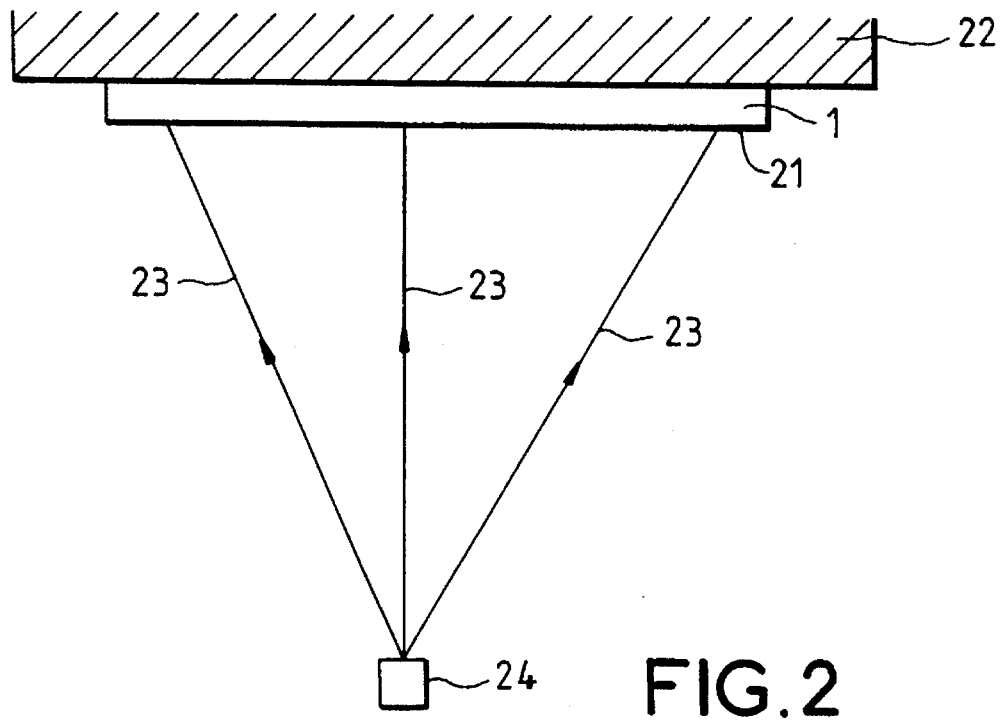
FIG. 2 is a drawing showing the principle of the hologram recording method for the making of the above-mentioned filter.

FIG. 2 shows a possible embodiment of a hologram such as this, with strata parallel to the support and with variable pitch.

To improve the stability, with the support 1 having one of its faces covered with a photosensitive material 21 for the recording of the hologram 2, a possible method consists in placing it in contact with a mirror 22, the reflection of the recording laser rays 23 coming from a source point 24 on the mirror 22 generating rays that interfere with the previous rays. This approach makes it possible to obtain a second emission source that is perfectly stable in relation to the support. The angle of incidence of each recording ray fixes the pitch of the strata and, consequently, the future filtered incident ray, for a given wavelength.

Figure 3:
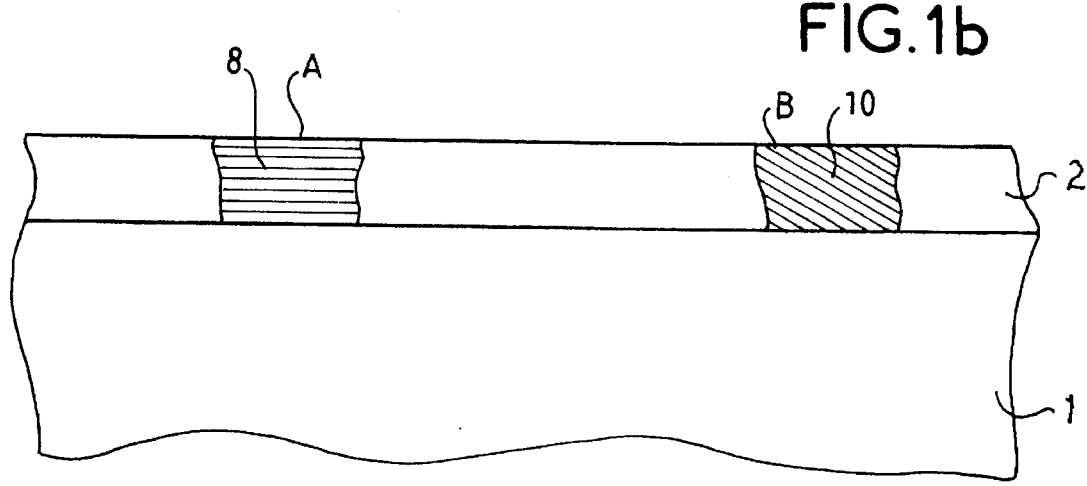
FIG. 3 shows another exemplary embodiment of a filter.

FIG. 3 shows another possible configuration of a filter in illustrating another possible variation of geometry of the strata of the hologram 2, where the orientation of the strata varies. In this embodiment, the pitch of the strata at the point A seen by the eye 3 along a direction that is normal to the support 1 is for example identical to the preceding case, of FIG. 1b, if the line to be filtered is the same. At the point 1, according to the relationship (1), the pitch $P_A$ is given by the following relationship:

$$p_A = \frac{\lambda}{2} \quad (2)$$

since at this point cos θ=1.

At the point B, the strata 1 have the same pitch as the strata 8 at the point A, but they are inclined with respect to the latter. The strata at the point B are all parallel to one another but they are inclined so as to be seen by the eye 3 along a direction perpendicular to their plane of inclination, the reason why the pitch of the strata at the point B is always given by the relationship (2). In this possible embodiment, the strata of the hologram 2 are oriented so as to be seen by the eye 3 along a direction perpendicular to their tangent plane, whatever may be the place at which they are located.

The configuration illustrated by FIG. 1b offers the advantage of being simple to record and leads notably to a hologram without unwanted images. However, it has a wide spectral width at the edge of the field, and permits limited range of movement by the eye or the sensor.

Figure 4:
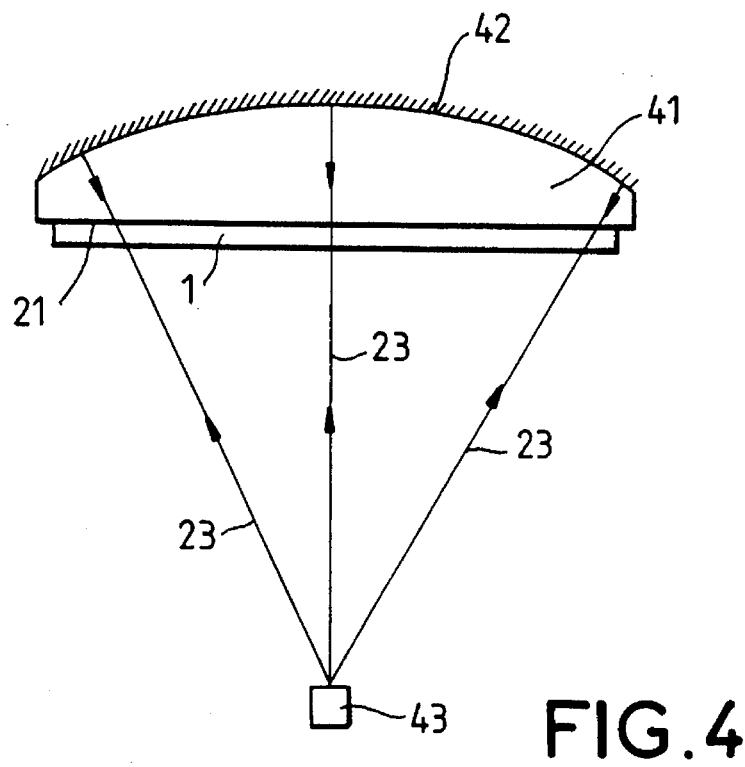
FIG. 4 is a drawing showing the principle of the hologram recording method for the making of the above-mentioned filter.

One method of recording strata for the making of the above embodiment is illustrated by a drawing of the principle of the invention presented in FIG. 4. The support 1 is covered on one of its faces by a photosensitive recording material 21, its other face being subjected to a radiation 23 of coherent light. The radiation 23 goes through the support 1 and the recording material 21, which is attached to a plano-convex lens 41, the convex face 42 of which is treated so as to be reflective. The curvature is such that any ray coming from the source 43 gets reflected normally on the convex face 42, corresponding to the recording of a spherical wave self-collimated at the center of a concave mirror. The selection of the filtered wavelength can be done by bringing the wavelength of the radiation 23 into play: this wavelength should be close to the protection wavelength.

The types of filter illustrated here above cannot be used to filter different wavelengths on different angular zones and therefore do not enable notably a sensor or a human eye to remain protected while at the same time being movable in relation to the filter.

Figure 5A:
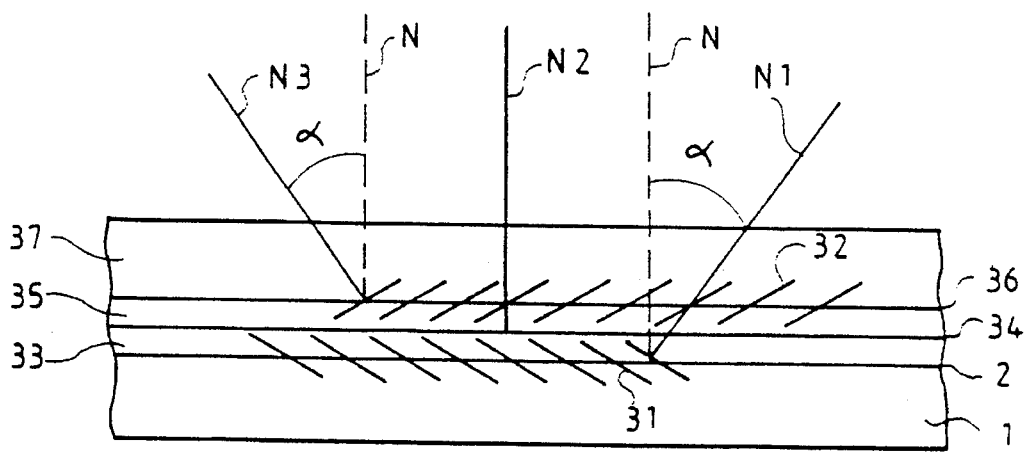
FIG. 5a shows an exemplary embodiment of a filter according to the invention, comprising a superimposition of holograms.

FIG. 5a illustrates a possible embodiment of a filter enabling the eye 3 or any other sensor to be protected and and to be movable in relation to the hologram, along an axis that is coplanar with the figure. To this end, the filter of FIG. 5a comprises a first support 1 covered with a first hologram 2, the strata of which, symbolized by lines 31, have a constant inclination, the normal N1 to these strata forming an angle α with the normal N of the support 1.

Figure 5B:
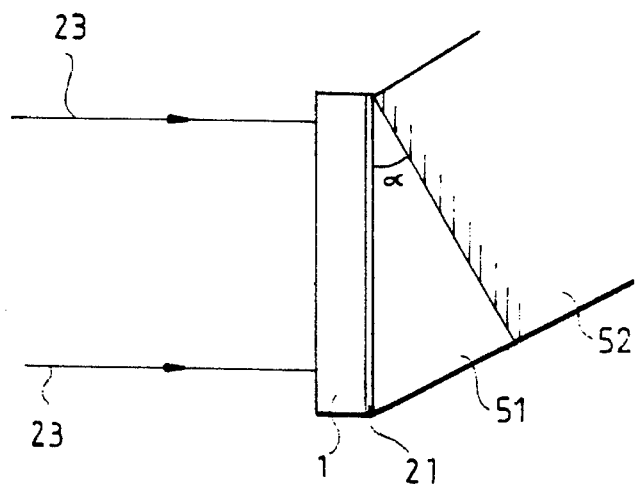
FIG. 5b is a drawing showing the principle of the hologram recording method for the making of the above-mentioned filter.

A method of recording inclined strata at a constant pitch is illustrated by the drawing of FIG. 5b showing the principle of the invention. The support 1 is covered on one of its faces with a photosensitive recording material 21, its other face being subjected to a radiation 23 of coherent light. The radiation 23 goes through the support 1 and the recording material 21, said recording material 21 being placed against a prism 51 having an angle α at the apex. The radiation is reflected at an angle 2α against a mirror 52, fixed to the prism 51. The interferences created by the incident rays reflected inside the prism 51 are recorded by the material 21 with strata inclined by an angle α with respect to the support.

On the first hologram 2 of FIG. 5a, there is superimposed a second hologram 34. These two holograms are, for example, fixed to each other by an optical bonder 33. The strata of the second hologram 34 are parallel to the support 1. Their normal N2 is therefore parallel to the normal N of the support 1 and their pitch is constant. This second hologram can be obtained according to the principle shown in FIG. 5b but in eliminating the prism, and it thus corresponds to the recording of a beam collimated on a mirror. The second hologram 34 is, for example, covered by a third hologram 36. These two holograms are, for example, joined by an optical bonder 35. The hologram 36, on a support 37, has inclined strata symbolized by the lines 32, identical for example to those of the first hologram 2 except, however, that their normal N3 forms an angle α with the normal N to the support 21 but is symmetrical with the normal N1 with respect to this normal N. The wavelengths filtered along the normal to the holograms 2, 34, 36 are identical.

The embodiment of FIG. 5a can be used to make the eye 3 movable with respect to the filter in parallel to the filter in the plane of the figure.

Each hologram has, in practice, an angular zone around its normal called a zone of angular acceptance where the eye or any other sensor can move while at the same time remaining protected from a radiation of a given wavelength. These zones, however, form an angle with a relatively small aperture and, consequently, only one zone offers little mobility to the eye 3.

This is the case with FIGS. 1b and 3 where a single hologram practically dictates that the eye should remain fixed with respect to the filter in order to be protected. The filter of FIG. 5a, in increasing the number of these zones of angular acceptance, enables a mobility of the eye 3 as can be seen in FIG. 5c.

Figure 5C:
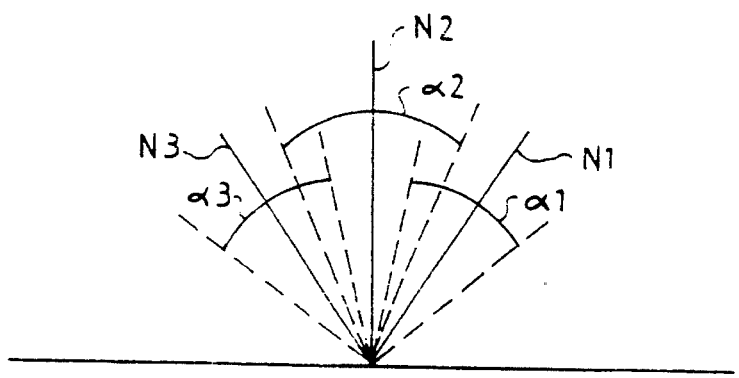
FIG. 5c shows angular acceptance zones of the above-mentioned filter.

FIG. 5c illustrates the zones of angular acceptance $a_1$, $a_2$, $a_3$ relating respectively to the holograms 2, 34, 36 each filtering, for example, the same wavelength. Provided that these zones overlap, as is the case in FIG. 5c, the eye can shift in the total zone of angular acceptance formed by the addition of these three angular zones $\alpha_1$, $\alpha_2$ and $\alpha_3$ while at the same time remaining protected from radiation along an axis coplanar with the figure.

The number of superimposed holograms could be increased in order to increase the total zone of angular acceptance, these holograms having strata that are inclined in varying degrees.

The exemplary embodiments of filters shown here above were single-line embodiments, i.e. they filtered the radiation in a band around a given wavelength, it being possible for the band to be as narrow as possible.

In a manner similar to that of the exemplary embodiment of FIG. 5b, it is possible to superimpose several holograms, while keeping within the acceptable limits of viewing quality. However, in this case, each hologram filters a given wavelength.

This enables the making of a multiple-line filter, filtering several wavelengths.

The holograms can then be made by means of according to a variable geometry of their strata similar to that of the first embodiment of FIG. 1b, i.e. by variation of the pitch of these strata, or similar to that of the second embodiment of FIG. 3, i.e. by variation of the inclination of the strata.

It is possible to combine the latter mode with the one presented by FIG. 5b and make a multiple-line filter.

To obtain efficiency for a filter that is of the type shown in FIG. 5a and contains at least two superimposed holograms, the optical bonder fixing the holograms to each other is, for example, associated with a selective absorbent material. This absorbent material is then selective for the radiation to be filtered for example. It may be a dye. This selective absorbent material has a low attenuation capacity and therefore attenuates the energy of a radiation crossing it to a small extent, this energy being, for example, diminished by a coefficient of attenuation of about 1/1000 during the passage of the radiation into the absorbent material. However, although it has no effect a priori, an absorbent material such as this may contribute to making the above-mentioned type of filter efficient.

Figure 6:
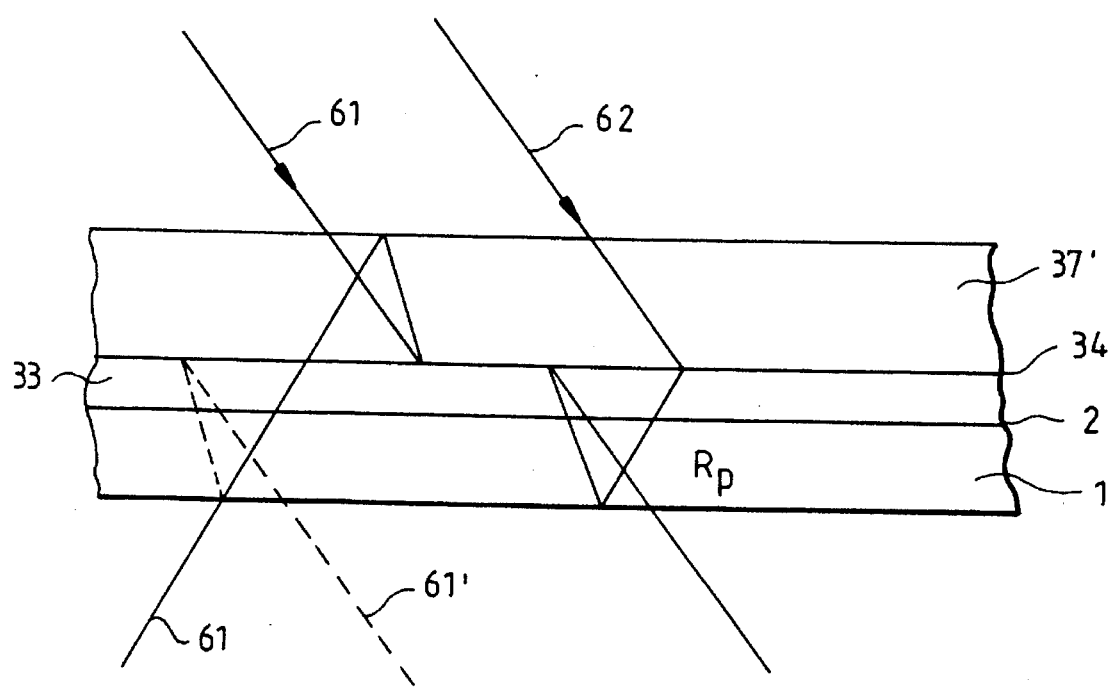
FIG. 6 shows reflections among holograms of a same filter.

Indeed, radiation reflected by the holograms may notably get reflected again on the internal face of the supports as shown in FIG. 6. The radiation then reaches the hologram at an angle for which, for example, it is not filtered. In this figure, a radiation 61 goes through a first support 37', made of glass for example, to reach a first hologram 34 on which it gets reflected. It is therefore filtered by this hologram 34. However, the reflected radiation gets reflected again on the internal face of the support 37'. The reflected radiation then encounters the first hologram 34 at an angle such that it is not filtered by this hologram. Similarly, and for the same reason, it goes through a second hologram 2 fixed to the first hologram by an optical bonder 33. At output of the second hologram 2, the radiation 61 may get reflected on the internal face of a second support 1, made of glass for example, to give a reflected radiation 61', shown in dashes, which gets reflected for example on the first hologram 34.

A second radiation 62, instead of getting reflected, may give a diffracted radiation $R_p$ at the first hologram 34 capable of producing unwanted images. This diffracted radiation may, for example, cross the second hologram 2, get reflected on the internal face of the second support 1 and then get reflected on the first hologram 34. Other examples of multiple reflections may occur between the holograms, notably in succession on the first hologram 34 and the second hologram 2. Each time that a radiation passes through the bonder 33, if this bonder is associated with a selective absorbent material, notably one that is absorbent for this radiation, then the radiation is attenuated by the coefficient of attenuation of the absorbent material. Multiple reflections then lead to multiple crossings of radiation and the effect of the absorbent material is then no longer negligible. Besides, the greater the number of layers of holograms contained in the filter, the better it performs and the more efficient it is, notably because of the layers of bonder that are associated with a selective absorbent material and are interposed between the holograms, the combination of the number of layers of bonders and of multiple reflections between the holograms increasing the attenuation capacity of the selective absorbent material associated with the bonder. This selective absorbent material makes it possible notably to attenuate unwanted radiation, like that illustrated in FIG. 6 and obtained from incident radiation 61, 62 on the first hologram 34.

The holograms may be of the type illustrated in FIGS. 1b or 3, or of any other type.

The hologram recording materials may be, for example, silver gelatine, dichromated gelatine or a photopolymer, all sensitive to the radiation against which protection is needed.

The supports 1, 37, 37' may be made, for example, of glass, plastic or any material transparent to the waves to be transmitted and enabling the implementation of the recording of the holograms according to methods known to those skilled in the art.

Finally, a filter according to the invention may be associated with another filter technique, notably a non-holographic technique, making use of thin layers for example.

What is claimed is:

1. A holographic filter for the protection of a sensor from radiation at a design wavelength of the filter, said filter comprising at least one support covered with at least two hologram layers, each hologram layer being constituted by a stack of strata, the strata of any one of the hologram layers being straight and being parallel with each other at all points, the strata of each stack being aligned such that the strata of one hologram layer are not parallel to the strata of any other hologram layer, the strata having zones of angular acceptance which overlap, said hologram layers being fixed to one another by an optical bonder associated with a selective absorbent material and positioned between successive ones of said hologram layers for selectively absorbing radiation at the design wavelength, said radiation at the design wavelength being internally reflected by surfaces of said holograms.

2. A filter according to claim 1, wherein the absorbent material is a dye.

3. A filter according to claim 1, wherein the strata seen by the sensor at a zero angle (A) are perpendicular to the normal to the support.

4. A filter according to claim 1, wherein the geometry of the strata is different from one hologram layer to the other.

5. A filter according to claim 1, wherein the support is made of glass.

6. A filter according to claim 1, wherein the support is made of plastic.

7. A filter according to claim 1, wherein the sensor is a human eye.

8. A filter according to claim 1, wherein the filtered radiation is laser radiation.

9. A holographic filter according to claim 1, wherein:

the number of holograms is sufficient to protect the sensor from the radiation at all angles and at any point along the filter, and the holograms are substantially flat.

10. A holographic filter comprising:

a plurality of transparent hologram layers, each one of said plurality of transparent hologram layers being formed by a stack of strata, said strata being straight and parallel for each one of said plurality of transparent hologram layers, said strata for each one of said plurality of transparent hologram layers not being parallel to said strata of any other one of said plurality of transparent hologram layers, said strata having a pitch for filtering damaging laser radiation at a design wavelength;

wherein, each one of said plurality of transparent hologram layers forms a zone of angular acceptance, each one of said plurality of transparent hologram layers filters said laser radiation at a design wavelength of said filter passing through the zones of angular acceptance at difference angles, said zones of angular acceptance overlap for ensuring that said laser radiation at said design wavelength does not penetrate through the holographic filter at obscure angles, and said zones of angular acceptances filter said laser radiation at all angles impinging on a surface of the holographic filter;

an optical bonder positioned between different ones of said plurality of transparent hologram layers for bonding each together and forming the holographic filter having each one of said plurality of transparent hologram layers stacked upon each other; and an absorbent material associated with the optical bonder and positioned along with said optical bonder between successive ones of said plurality of transparent hologram layers for absorbing reflected laser radiation being internally reflected by inner surfaces of said plurality of transparent hologram layers defined by those surfaces of said plurality of transparent hologram layers which are in contact with said optical bonder, and thereby preventing a danger that said laser radiation will penetrate through the holographic filter at angles outside the zones of angular acceptance.

* * * * *